(12) United States Patent
Okuya

(10) Patent No.: US 10,980,463 B2
(45) Date of Patent: Apr. 20, 2021

(54) DRIVER'S TENSION LEVEL DETERMINING APPARATUS AND DRIVER'S TENSION LEVEL DETERMINING METHOD

(71) Applicant: DENSO IT LABORATORY, INC., Tokyo (JP)

(72) Inventor: Tomokatsu Okuya, Tokyo (JP)

(73) Assignee: DENSO IT LABORATORY, INC., Tokyo (JP)

( * ) Notice: Subject to any disclaimer, the term of this patent is extended or adjusted under 35 U.S.C. 154(b) by 625 days.

(21) Appl. No.: 15/465,784

(22) Filed: Mar. 22, 2017

(65) Prior Publication Data

US 2017/0311865 A1  Nov. 2, 2017

(30) Foreign Application Priority Data

Apr. 27, 2016  (JP) .............................. JP2016-088943

(51) Int. Cl.
*A61B 5/18* (2006.01)
*A61B 5/00* (2006.01)
*B60W 40/08* (2012.01)

(52) U.S. Cl.
CPC .............. *A61B 5/18* (2013.01); *A61B 5/6893* (2013.01); *A61B 5/72* (2013.01); *A61B 5/7242* (2013.01);
(Continued)

(58) Field of Classification Search
CPC ........... A61B 5/18; A61B 5/6893; A61B 5/72; B60W 40/08; B60W 2040/0872;
(Continued)

(56) References Cited

U.S. PATENT DOCUMENTS 7,321,842 B2 * 1/2008 Shiomi ................... G10L 17/26
702/181
7,470,231 B2 * 12/2008 Fujita ....................... A61B 5/18
600/300

(Continued)

FOREIGN PATENT DOCUMENTS

JP         4100002 B2 *  6/2008
JP       2015-189402 A    11/2015

OTHER PUBLICATIONS

Sano (M. Sano and Y. Sawada, "Measurement of the Lyapunov Spectrum from a Chaotic Time Series", Physical Review Letters, vol. 55, No. 10, Sep. 2, 1985) (Year: 1985).*

(Continued)

*Primary Examiner* — Alexander Satanovsky
*Assistant Examiner* — Douglas Kay
(74) *Attorney, Agent, or Firm* — Louis Woo

(57) ABSTRACT

Disclosed is a technique of determining a driver's tension level (tension state degree) in vehicle driving in detail with a simple configuration. According to the technique, a nonlinear analyzing unit 110 of a driver's tension level determining apparatus 100 determining the tension level in driving of a driver acquires the driving operation amounts relating to driving operations of a driver (the operation amounts relating to operations of an accelerator pedal, a brake pedal, a handle, and the like), and then calculates the Lyapunov exponents about the driving operation amounts by performing nonlinear analysis processing. A frequency spectrum analyzing unit 120 calculates the power spectral density of time series data of the Lyapunov exponents, and then calculates an integrated value of a predetermined low frequency band in the calculated power spectral density. A driver's tension level determining unit 130 determines that the driver's tension level is any one of an excessive tension state, a moderate tension state, and an insufficient tension state using the integrated value of the predetermined low frequency band.

6 Claims, 17 Drawing Sheets

(52) U.S. Cl.
CPC .......... *A61B 5/7282* (2013.01); *B60W 40/08* (2013.01); *B60W 2040/0872* (2013.01); *B60W 2540/10* (2013.01); *B60W 2540/12* (2013.01); *B60W 2540/18* (2013.01); *B60W 2540/22* (2013.01)

(58) Field of Classification Search
CPC ......... B60W 2540/10; B60W 2540/12; B60W 2540/18; B60W 2540/22
USPC .......................................................... 702/76
See application file for complete search history.

(56) References Cited

U.S. PATENT DOCUMENTS

| | | | | |
|---|---|---|---|---|
| 7,663,495 | B2 * | 2/2010 | Haque | B60K 28/066 180/272 |
| 2006/0265444 | A1 * | 11/2006 | Shiomi | G10L 17/26 708/446 |
| 2007/0078351 | A1 * | 4/2007 | Fujita | A61B 5/18 600/500 |
| 2007/0080816 | A1 * | 4/2007 | Haque | B60K 28/066 340/576 |
| 2007/0174377 | A2 * | 7/2007 | Shiomi | G10L 17/26 708/446 |
| 2011/0230792 | A1 * | 9/2011 | Sarig-Bahat | A61B 5/1124 600/595 |
| 2015/0088024 | A1 * | 3/2015 | Sackellares | A61B 5/0476 600/544 |
| 2017/0364070 | A1 * | 12/2017 | Oba | B60W 50/08 |
| 2018/0194365 | A1 * | 7/2018 | Bae | B60W 40/08 |
| 2019/0143036 | A1 * | 5/2019 | Dumont | A61M 5/172 |

OTHER PUBLICATIONS

Posada-Quintero (H. F. Posada-Quintero and K. H. Chon, "Frequency-Domain Electrodermal Activity Index of Sympathetic Function", 2016 IEEE-EMBS International Conference on Biomedical and Health Informatics (BHI) pp. 497-500, Feb. 1, 2016) (Year: 2016).*

* cited by examiner

FIG. 5
SENSING INFORMATION
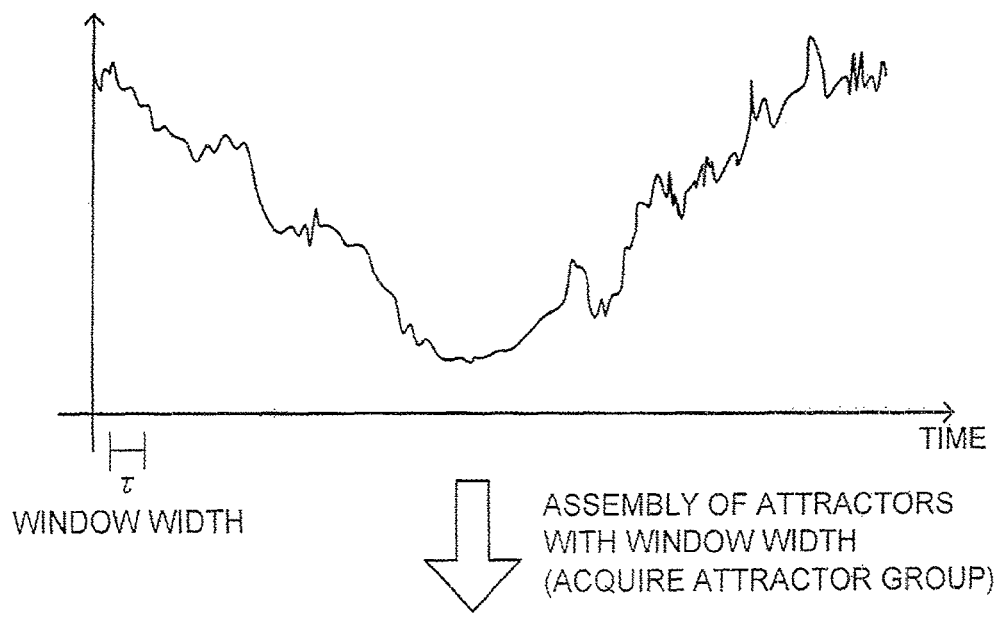
WINDOW WIDTH $\tau$
⬇ ASSEMBLY OF ATTRACTORS WITH WINDOW WIDTH (ACQUIRE ATTRACTOR GROUP)
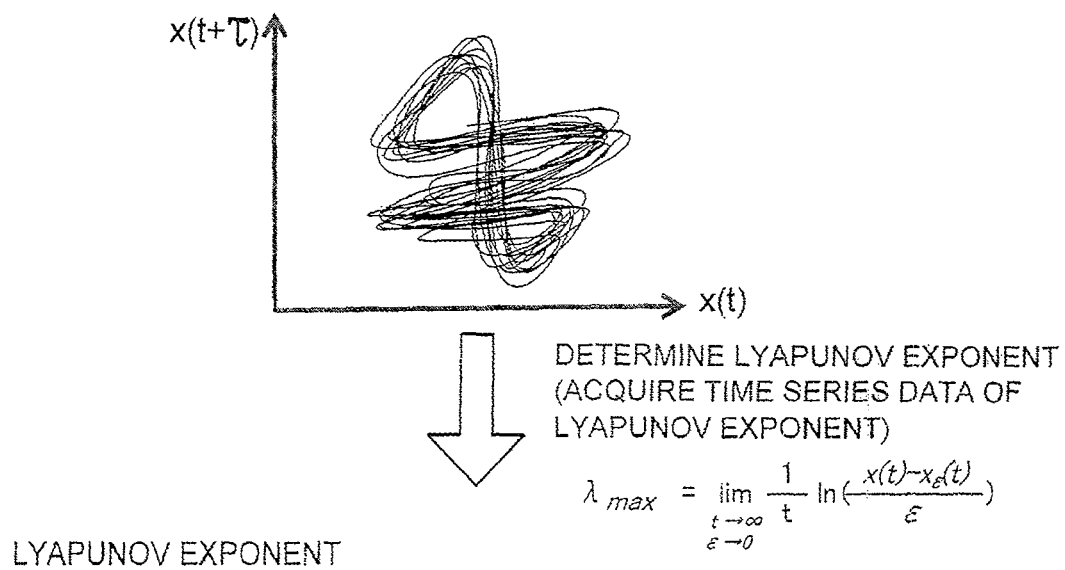
⬇ DETERMINE LYAPUNOV EXPONENT (ACQUIRE TIME SERIES DATA OF LYAPUNOV EXPONENT)
$$\lambda_{max} = \lim_{\substack{t \to \infty \\ \varepsilon \to 0}} \frac{1}{t} \ln \left( \frac{x(t) - x_\varepsilon(t)}{\varepsilon} \right)$$
LYAPUNOV EXPONENT
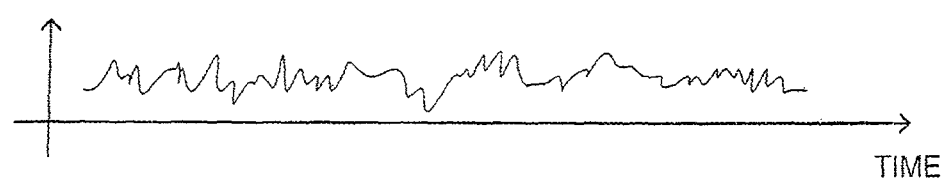
TIME (1) TIME SERIES DATA OF LYAPUNOV EXPONENT (2) POWER SPECTRAL DENSITY (SAMPLING RATE = 10 SECONDS)

FIG. 8

WHEN TIME SERIES DATA OF LF/HF ARE
$A_1, A_2, A_3, \cdots, A_N$, AND
TIME SERIES DATA OF HF ARE
$B_1, B_2, B_3, \cdots, B_N$, NORMALIZED LF/HF $= (A_i - m_A)/(2\sigma_A)$
NORMALIZED HF $= (B_i - m_B)/(2\sigma_B)$

WHEREIN $$m_A = \frac{1}{N}\sum_{i=1}^{N} A_i$$

$$m_B = \frac{1}{N}\sum_{i=1}^{N} B_i$$

$$\sigma_A = \sqrt{\frac{1}{N}\sum_{i=1}^{N}(A_i - m_A)^2}$$

$$\sigma_B = \sqrt{\frac{1}{N}\sum_{i=1}^{N}(B_i - m_B)^2}$$

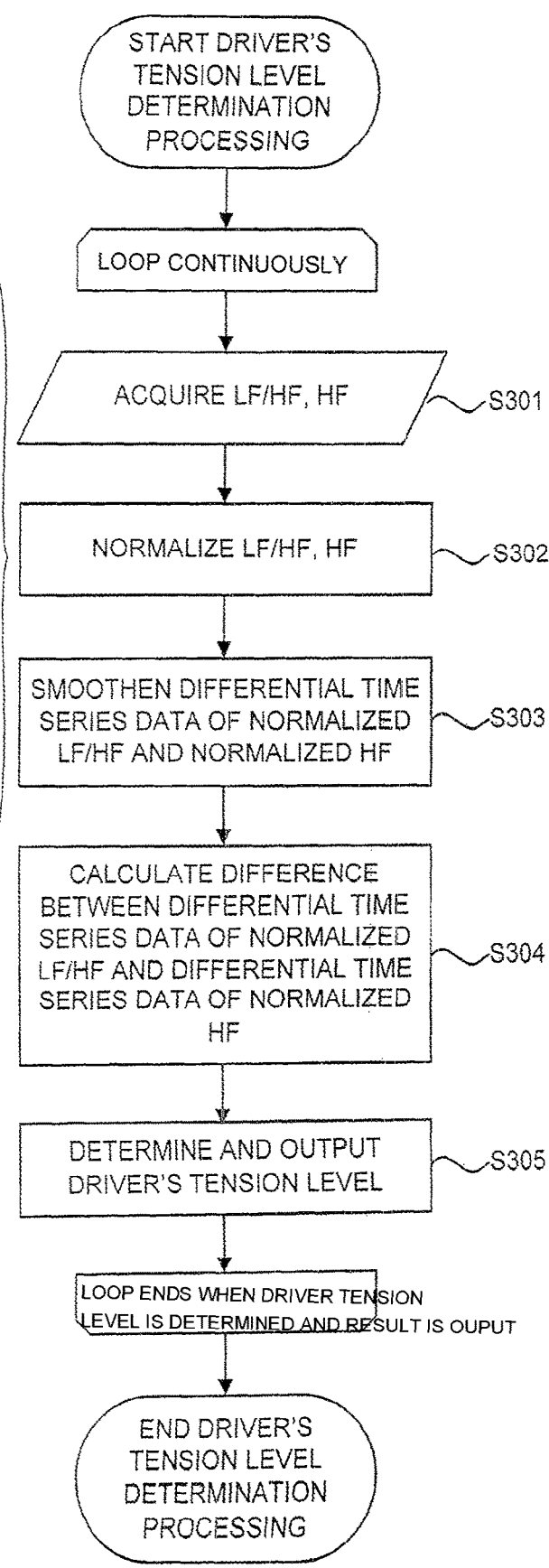

START DRIVER'S TENSION LEVEL DETERMINATION PROCESSING

LOOP CONTINUOUSLY

ACQUIRE LF/HF, HF — S301

NORMALIZE LF/HF, HF — S302

SMOOTHEN DIFFERENTIAL TIME SERIES DATA OF NORMALIZED LF/HF AND NORMALIZED HF — S303

CALCULATE DIFFERENCE BETWEEN DIFFERENTIAL TIME SERIES DATA OF NORMALIZED LF/HF AND DIFFERENTIAL TIME SERIES DATA OF NORMALIZED HF — S304

DETERMINE AND OUTPUT DRIVER'S TENSION LEVEL — S305

LOOP ENDS WHEN DRIVER TENSION LEVEL IS DETERMINED AND RESULT IS OUPUT

END DRIVER'S TENSION LEVEL DETERMINATION PROCESSING

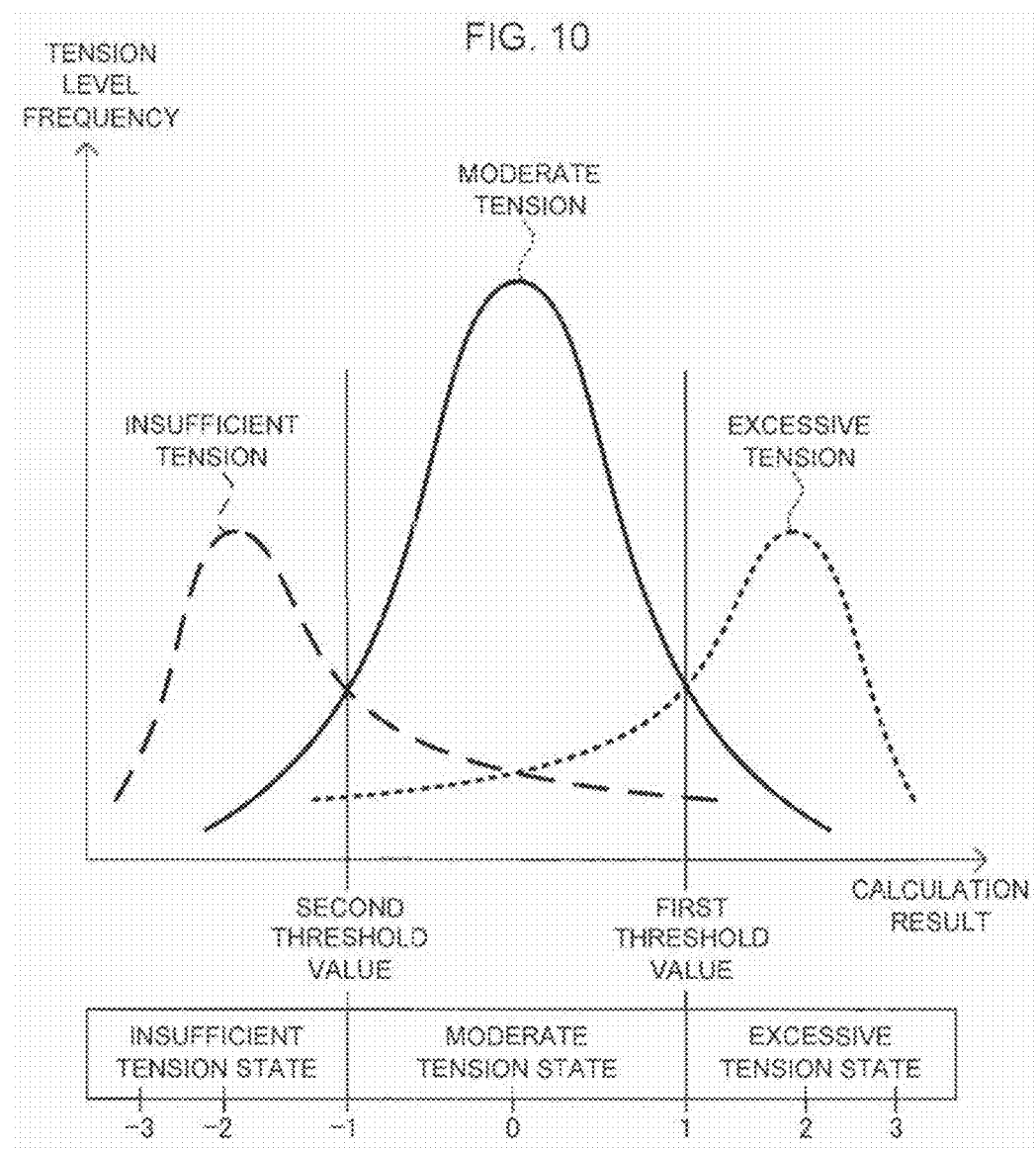

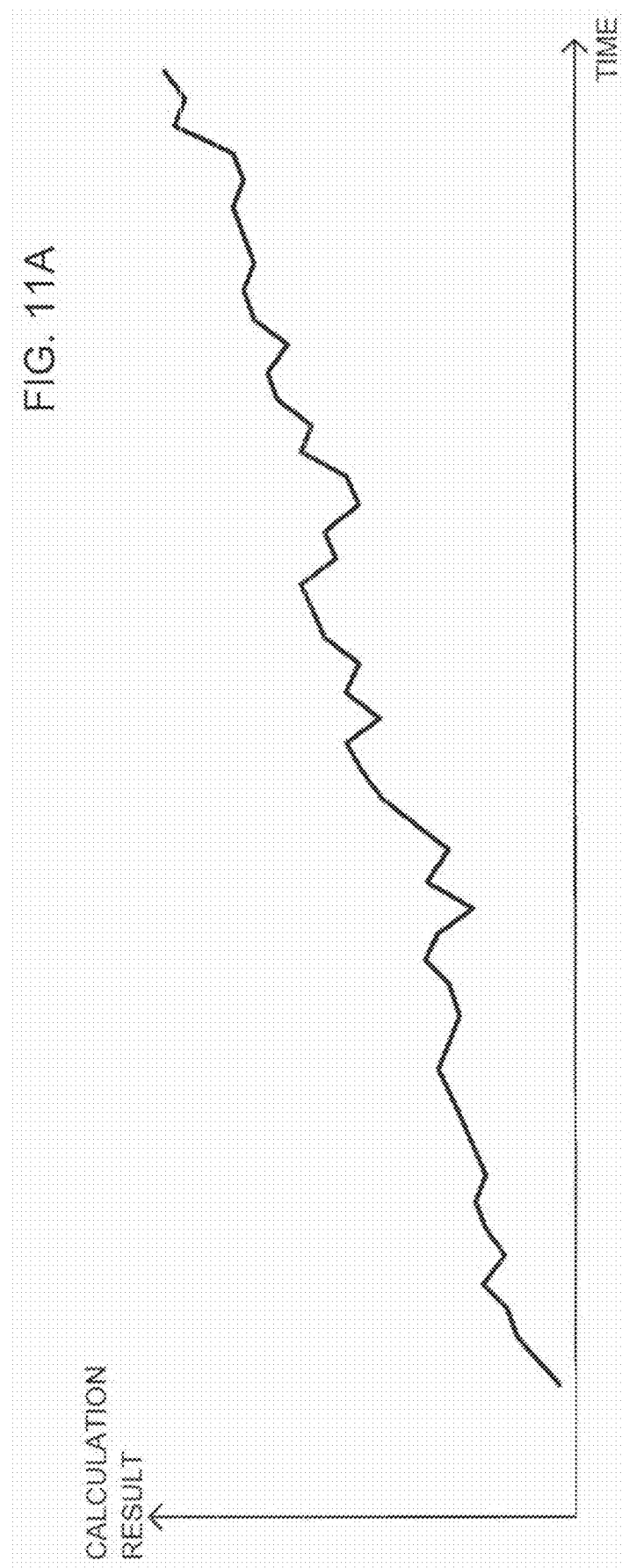

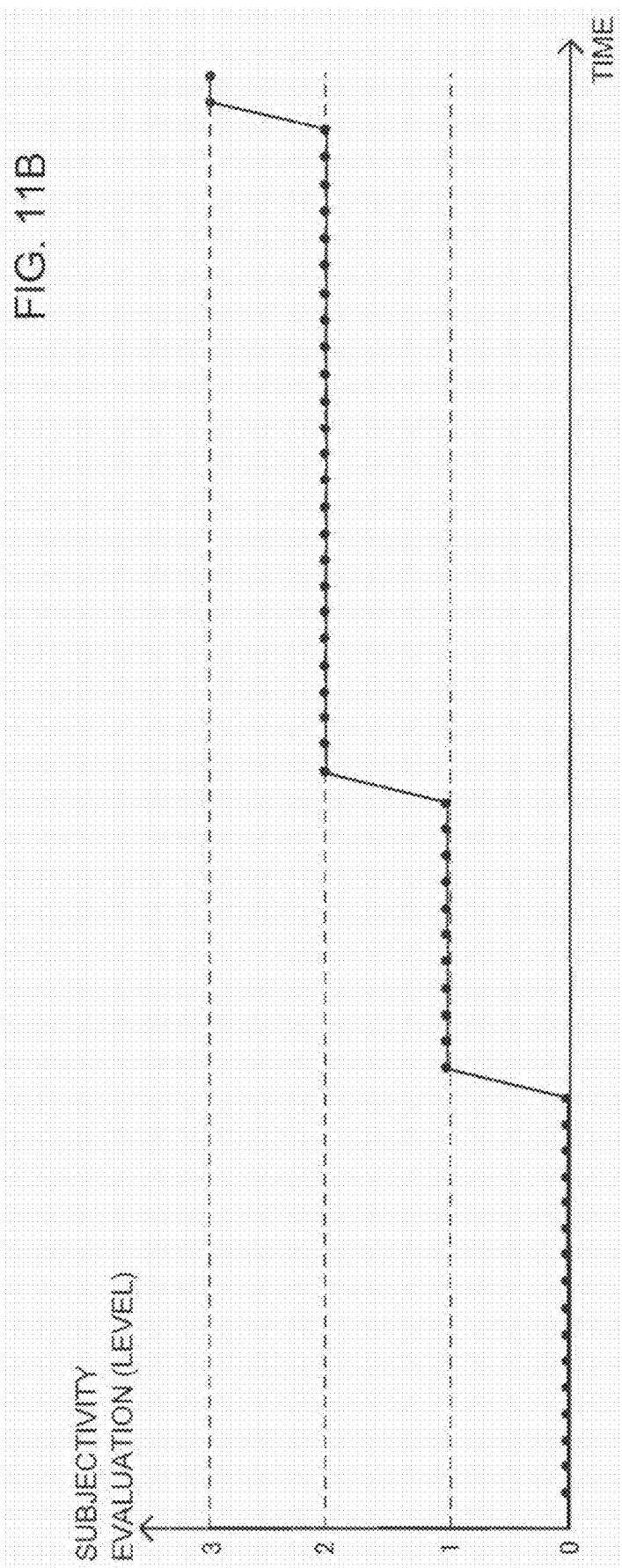

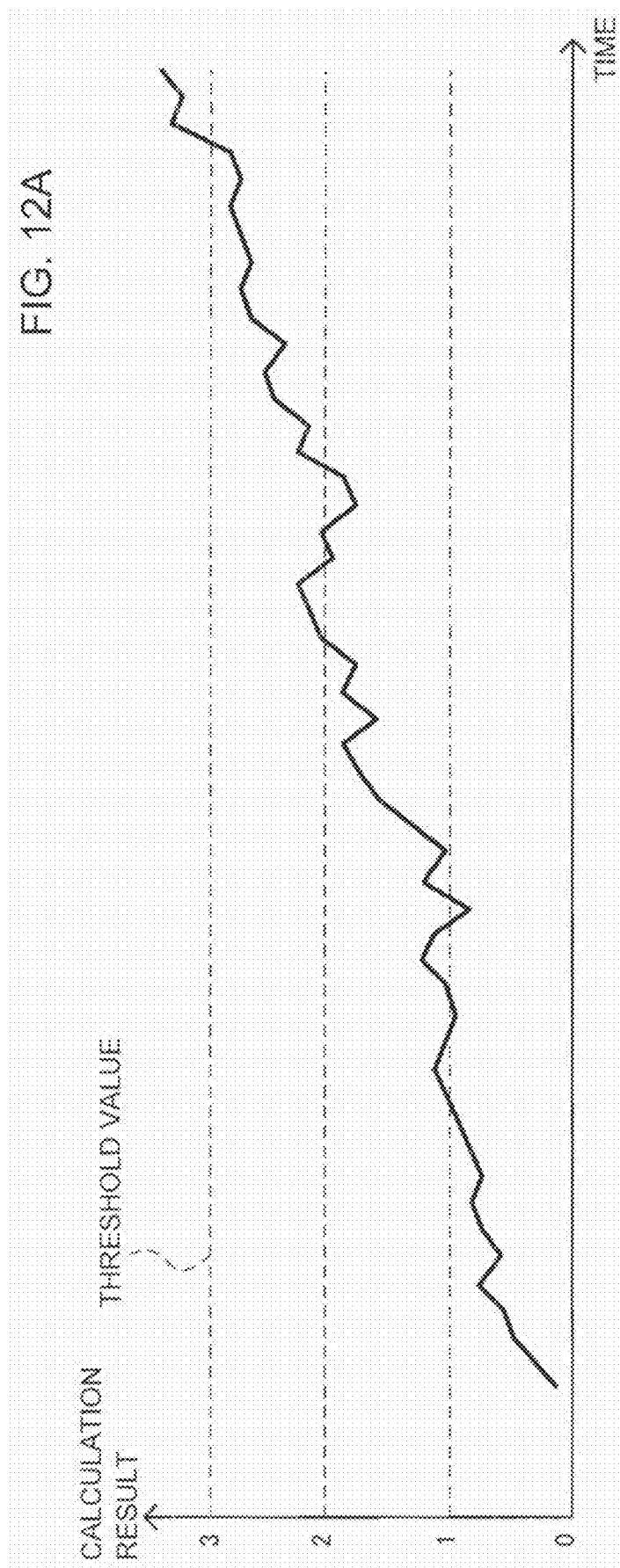

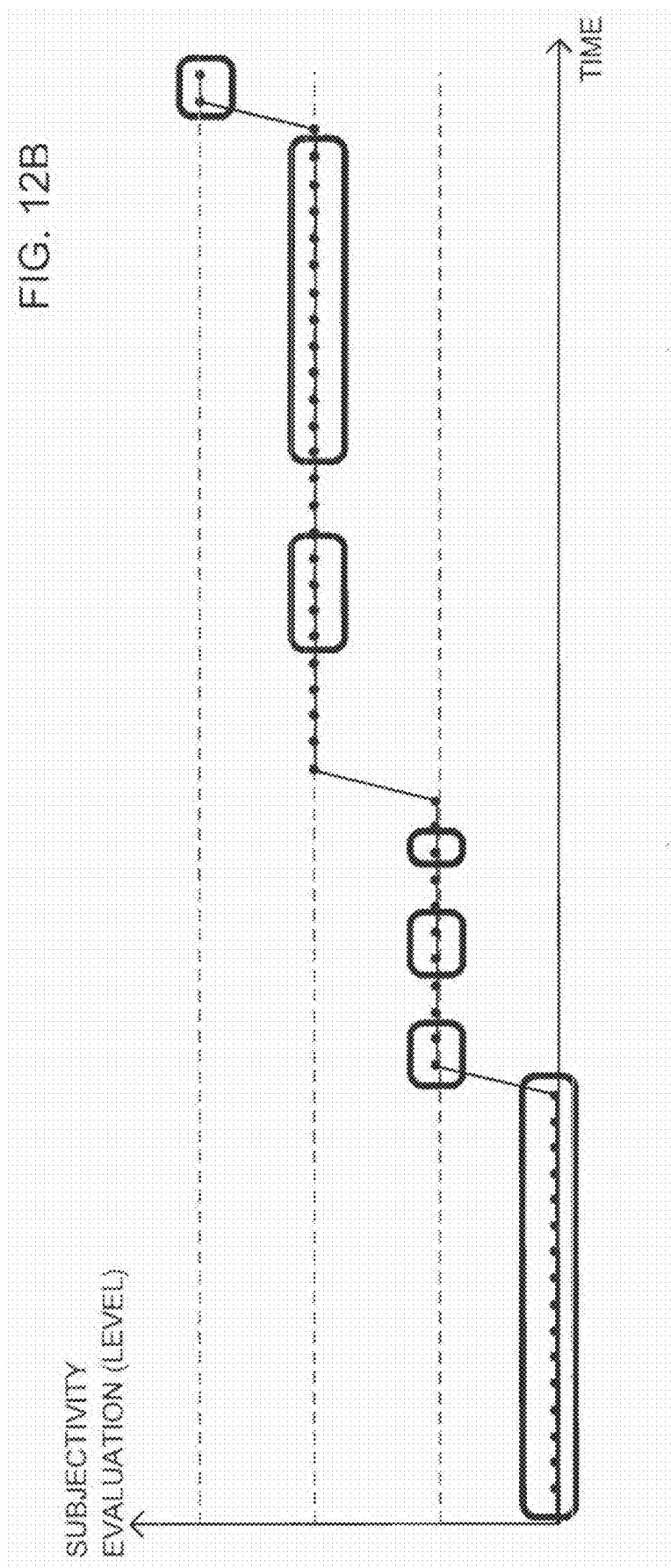

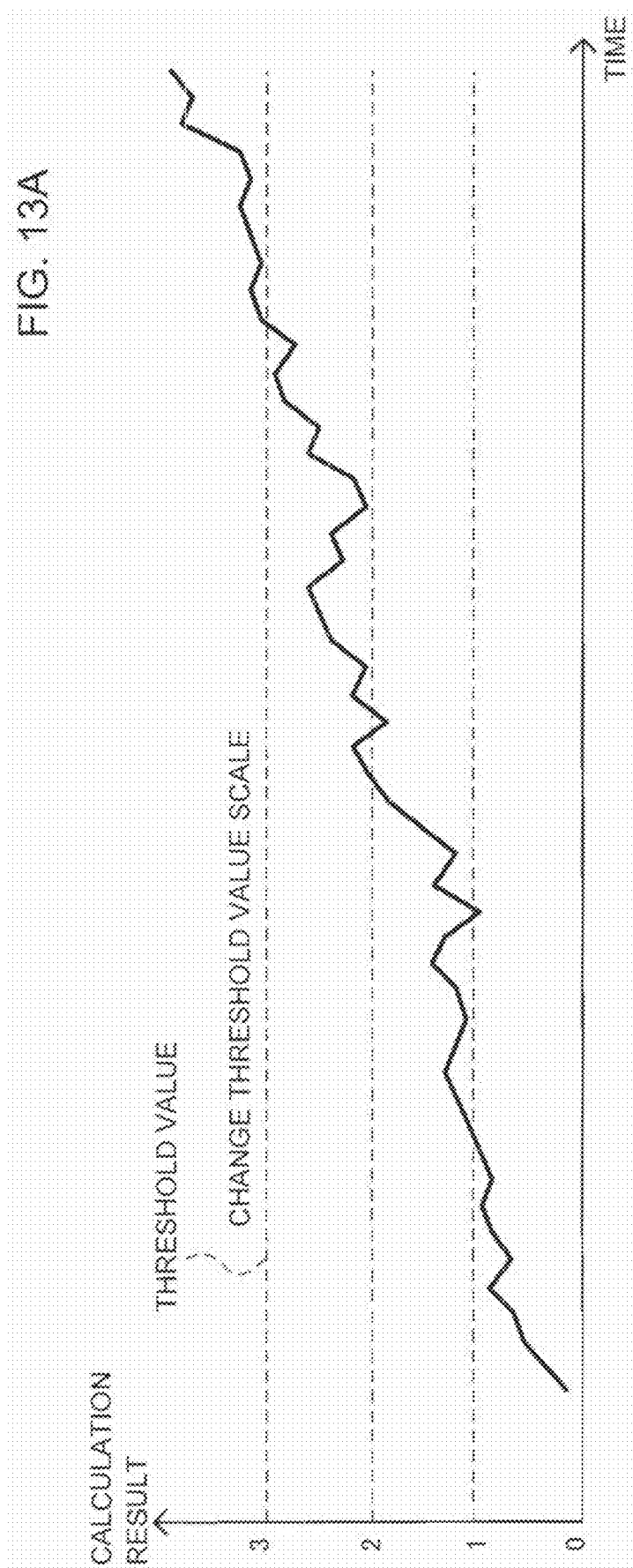

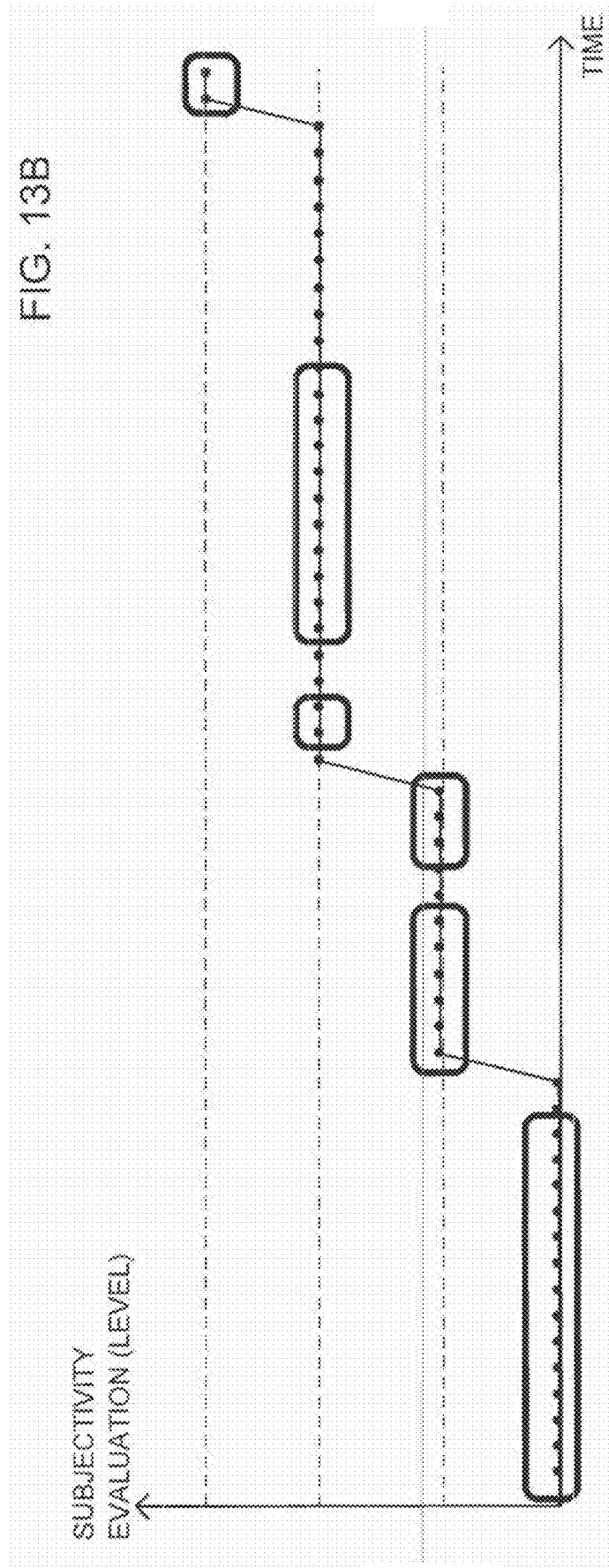

DRIVER'S TENSION LEVEL DETERMINING APPARATUS AND DRIVER'S TENSION LEVEL DETERMINING METHOD

TECHNICAL FIELD

The present invention relates to a technique of determining a driver's tension level (tension state degree) in vehicle driving.

BACKGROUND ART

For example, Patent Document 1 mentioned below discloses a technique of determining the driver's tension level in vehicle driving with a simple configuration based on the driving operation amounts relating to driving operations (operation amounts relating to operations of an accelerator pedal, a brake pedal, a handle, and the like) of a driver.

[Patent Document 1]

Japanese Patent Application Publication No. 2015-189402

SUMMARY OF THE INVENTION

However, Patent Document 1 does not necessarily clearly disclose the determination of the tension level. It is an object of the present invention to provide a driver's tension level determining apparatus and a driver's tension level determining method capable of determining the driver's tension level in vehicle driving in detail with a simple configuration in view of the above-described problems.

In order to achieve the object, the present invention provides a driver's tension level determining apparatus which determines a tension state degree in driving of a driver driving a vehicle and which has a nonlinear analyzing unit acquiring the driving operation amount relating to a driving operation of the driver, and then calculating the Lyapunov exponent relating to the driving operation amount by performing nonlinear analysis processing, a frequency spectrum analyzing unit calculating the power spectral density of time series data of the Lyapunov exponent, and then calculating an integrated value of a predetermined low frequency band in the calculated power spectral density, and a driver's tension level determining unit determining that the tension state of the driver is any of an excessive tension state, a moderate tension state, and an insufficient tension state using the integrated value of the predetermined low frequency band.

Moreover, in order to achieve the object, the present invention provides a driver's tension level determining method which determines a tension state degree in driving of a driver driving a vehicle and which includes a nonlinear analyzing step of acquiring the driving operation amount relating to a driving operation of the driver, and then calculating the Lyapunov exponent relating to the driving operation amount by performing nonlinear analysis processing, a frequency spectrum analyzing step of calculating the power spectral density of time series data of the Lyapunov exponent, and then calculating an integrated value of a predetermined low frequency band in the calculated power spectral density, and a driver's tension level determining step of determining that the tension state of the driver is any of an excessive tension state, a moderate tension state, and an insufficient tension state using the integrated value of the predetermined low frequency band.

The present invention has the configuration described above and demonstrates an effect that the driver's tension level in vehicle driving can be determined in detail with a simple configuration based on information relating to the operation amounts of usual vehicle driving operations (operations of an accelerator pedal, a brake pedal, a handle, and the like) of a driver.

BRIEF DESCRIPTION OF THE DRAWINGS

FIG. 5 is a view showing an example of a specific calculation method of the fluctuation analysis processing in the embodiment of the present invention.

FIG. 8 is a flow chart showing an example of determination processing of a tension level in the embodiment of the present invention.

FIG. 10 is an example of a graph for determining a first threshold value and a second threshold value serving as the standard for determining a driver's tension level in the embodiment of the present invention.

FIG. 11A is an example of data for use in processing for determining threshold values in the embodiment of the present invention and is a graph showing the calculation result obtained from the access pedal stepping amount in one driving of a specific test subject (driver).

FIG. 11B is an example of data for use in processing for determining threshold values in the embodiment of the present invention and is a graph showing the subjectivity of a tension level which the specific test subject felt in driving.

FIG. 12A is a view showing the state where threshold values for levels 0 to 3 are set to specific calculation result values in the graph shown in FIG. 11A.

FIG. 12B is a view schematically showing the matching degree of the subjectivity of the tension level which the specific test subject felt shown in FIG. 11B defined as a correct value and the evaluation level estimated from the threshold values shown in FIG. 12A.

FIG. 13A is a view showing the state where different threshold values are set in the graph shown in FIG. 12A.

FIG. 13B is a view schematically showing the matching degree of the subjectivity of the tension level which the specific test subject felt shown in FIG. 11B defined as a correct value and the evaluation level estimated from the threshold values shown in FIG. 13A.

DESCRIPTION OF THE EMBODIMENTS

Hereinafter, an embodiment of the present invention is described with reference to the drawings.

The present invention analyzes the active state of the sympathetic nerve and the parasympathetic nerve in the autonomic nerves of a driver based on information relating to operation amounts of vehicle driving operations of a driver to determine the driver's tension level (tension state degree) in vehicle driving from time series changes of the analysis result. Herein, it is determined that the tension state degree in vehicle driving of a driver is any one of a moderate tension state (moderate tension state to vehicle driving), an excessive tension state where the tension level is higher than that of the moderate tension state (excessively high tension state to vehicle driving), and an insufficient tension state where the tension level is lower than that of the moderate tension state (insufficient tension state to vehicle driving) and at least these three tension states can be expressed by the degree on one axis. For example, an aspect is mentioned in which, the moderate tension state is defined as Lv0 (Level 0), the excessive tension state is set as a degree on the plus side (the level rises from Lv1 (Level 1) according to the severity) and the insufficient tension state is set as a degree on the minus side (the level decreases from Lv−1 (Level−1) according to the severity). The driver's tension level in vehicle driving is determined by the aspect. The driver's tension level in vehicle driving is determined considering the characteristics relating to the tension of each driver. The characteristics relating to the tension of each driver is different in each driver. For example, the zone of the moderate tension state, i.e., the boundary where the tension level enters Lv1 of the excessive tension state from Lv0 of the moderate tension state and the boundary where the tension level enters Lv−1 of the insufficient tension state from Lv0 of the moderate tension state, is different in each driver. Therefore, the present invention enables learning of the above-described boundaries corresponding to each driver from the state of the autonomic nerves in daily safe driving in the past.

Figure 1:
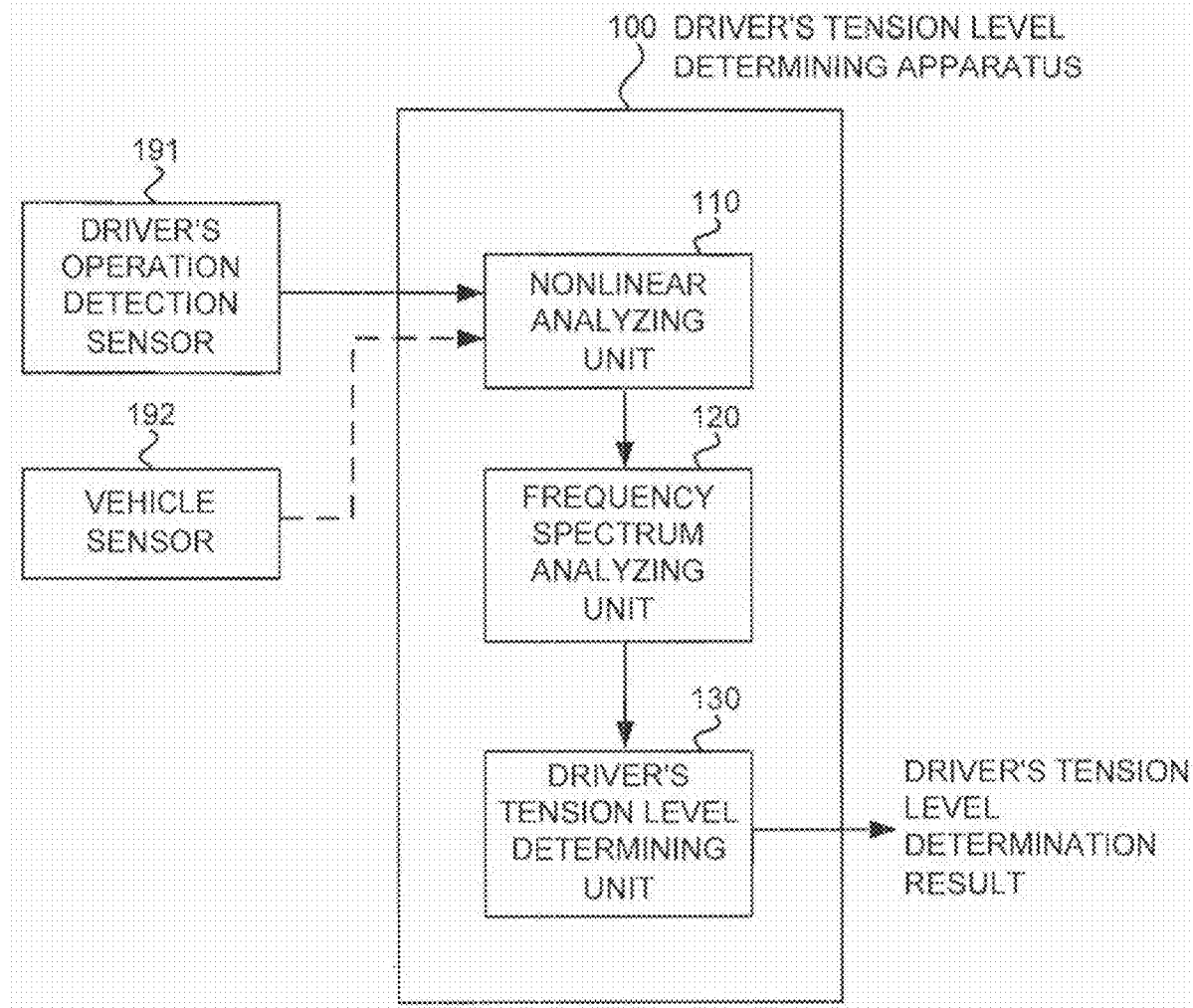
FIG. 1 is a block diagram showing an example of a driver's tension level determining apparatus in an embodiment of the present invention.

First, an example of the configuration of a driver's tension level determining apparatus in the embodiment of the present invention is described. FIG. 1 is a block diagram showing an example of the driver's tension level determining apparatus in the embodiment of the present invention.

A driver's tension level determining apparatus 100 shown in FIG. 1 has a nonlinear analyzing unit 110, a frequency spectrum analyzing unit 120, and a driver's tension level determining unit 130. In FIG. 1, each function is shown by a block but these functions are realizable by hardware and/or a program (program executable by a computer including a processor and a memory).

The nonlinear analyzing unit 110 has a function of receiving sensing information including driving operation amounts relating to driving operations of a driver driving a vehicle from a driver's operation detection sensor 191 monitoring the driving operation amounts, and then performing nonlinear analysis processing to the sensing information.

As the driver's operation detection sensor 191, a sensor detecting the accelerator pedal stepping amount (stepping angle, stepping power, and the like), a sensor detecting a brake pedal stepping amount (stepping angle, stepping power, and the like), a sensor detecting a handle operation distance (steering distance (for example, steering amount grasped from the rotation angle and the like of the handle), torque, and the like of the handle), and the like are usable, for example. As the sensing information, vehicle state information output from a vehicle sensor 192 detecting the traveling state of a vehicle (for example, a vehicle speed sensor measuring the vehicle speed or an acceleration sensor determining the acceleration of a vehicle) may be used. Moreover, the throttle opening degree obtained from a vehicle signal may be used as a substitute for the accelerator pedal stepping amount.

Specifically, the nonlinear analyzing unit 110 has a function of acquiring the sensing information detected in the driver's operation detection sensor 191 (for example, the accelerator pedal stepping amount detected in the sensor detecting the accelerator pedal stepping amount described above) on the millisecond order (millisecond unit), generating an attractor of the acquired sensing information (or part of the sensing information processed or extracted for calculation) as the driving feature amount of a driver, and then performing fluctuation analysis processing of the calculated result (generated attractor of the driving feature amount) to calculate the Lyapunov exponents relating to the driving feature amount.

The frequency spectrum analyzing unit 120 has a function of acquiring the Lyapunov exponents calculated in the nonlinear analyzing unit 110, determining the power spectral density of time series data of the Lyapunov exponents based on a frequency spectrum analyzing technique, and then calculating a value of the power spectral density of each of a low frequency band and a high frequency band from the power spectral density.

The driver's tension level determining unit 130 has a function of determining the driver's tension level using the value of the power spectral density of each of the low frequency band and the high frequency band calculated in the frequency spectrum analyzing unit 120. The driver's tension level determining unit 130 can determine that the tension level (tension state degree) of a driver is any one of the excessive tension state, the moderate tension state, and the insufficient tension state. The driver's tension level determining unit 130 may independently include each of a configuration of determining the excessive tension state (excessive tension state determining unit), a configuration of determining the insufficient tension state (insufficient tension state determining unit), and a configuration of determining the moderate tension state (moderate tension state determining unit) for the determination of the driver's tension level.

FIG. 1 shows the state where the driver's tension level determining apparatus 100 includes all the functions of the nonlinear analyzing unit 110, the frequency spectrum analyzing unit 120, and the driver's tension level determining unit 130. However, a part of or all of the nonlinear analyzing unit 110, the frequency spectrum analyzing unit 120, and the driver's tension level determining unit 130 may be realized by an independent apparatus (computer). For example, the sensing information output from the driver's operation detection sensor 191 (further the vehicle state information output from the vehicle sensor 192) may be written once on a memory, and then the nonlinear analyzing unit 110 may read the sensing information (further the vehicle state information) written on the memory to perform nonlinear analysis processing. Similarly, the Lyapunov exponents output from the nonlinear analyzing unit 110 may be written once on a memory, and then the frequency spectrum analyzing unit 120 may read the Lyapunov exponents written on the memory to perform frequency spectrum analysis processing. Similarly, the power spectral density value of each of the low frequency band and the high frequency band output from the frequency spectrum analyzing unit 120 may be written once on a memory, and then the driver's tension level determining unit 130 may read the value of the power spectral density of each of the low frequency band and the high frequency band written on the memory to perform driver's tension level determination processing.

Figure 2:
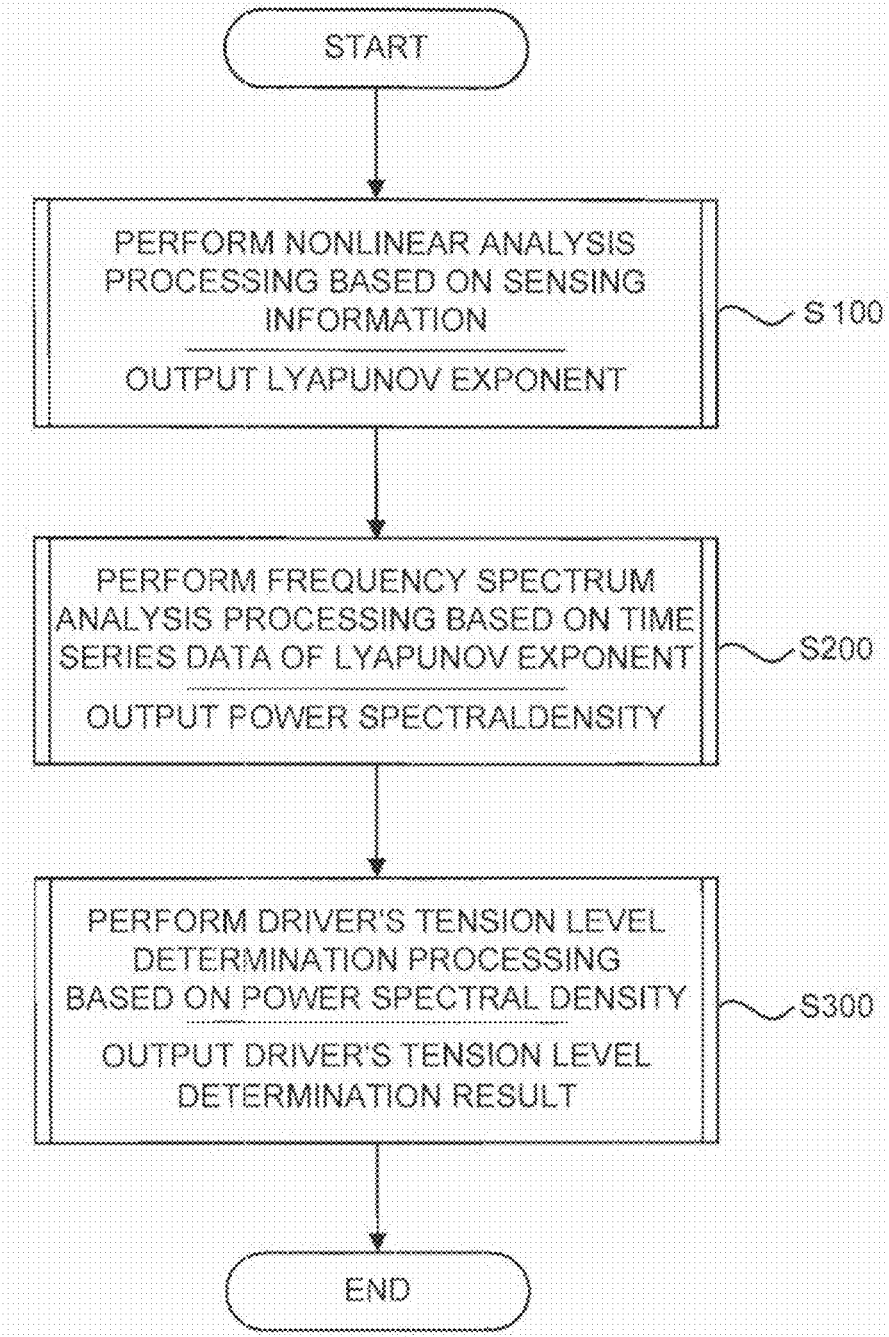
FIG. 2 is a flow chart showing an example of data processing of the driver's tension level determining apparatus in the embodiment of the present invention.

Next, an example of data processing of the driver's tension level determining apparatus 100 in the embodiment of the present invention is described based on the driver's tension level determining apparatus 100 shown in FIG. 1. FIG. 2 is a flow chart showing an example of data processing of the driver's tension level determining apparatus 100 in the embodiment of the present invention.

In the driver's tension level determining apparatus 100 in the embodiment of the present invention, the nonlinear analyzing unit 110 first performs nonlinear analysis processing based on the sensing information detected in and output from the driver's operation detection sensor 191 (further the vehicle state information output from the vehicle sensor 192 may be taken into consideration) to calculate and output the Lyapunov exponents (Step S100). Next, the frequency spectrum analyzing unit 120 performs frequency spectrum analysis processing based on the Lyapunov exponents output from the nonlinear analyzing unit 110 to calculate and output a value of the power spectral density of each of a low frequency band and a high frequency band (Step S200). Then, the driver's tension level determining unit 130 performs driver's tension level determination processing based on the value of the power spectral density of each of the low frequency band and the high frequency band output from the frequency spectrum analyzing unit 120 to output a driver's tension level determination result (Step S300).

Hereinafter, an example of the processing of each of the steps S100 to S300 shown in FIG. 2 is described.

Figure 3:
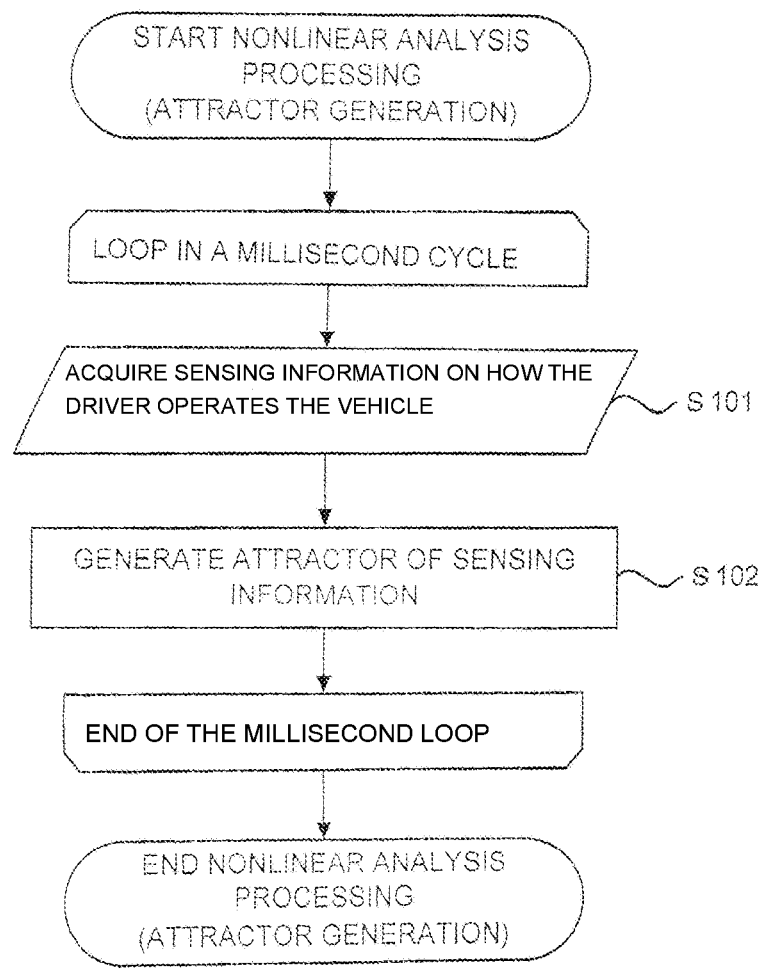
FIG. 3 is a flow chart showing an example (attractor generation processing) of nonlinear analysis processing in the embodiment of the present invention.
Figure 4:
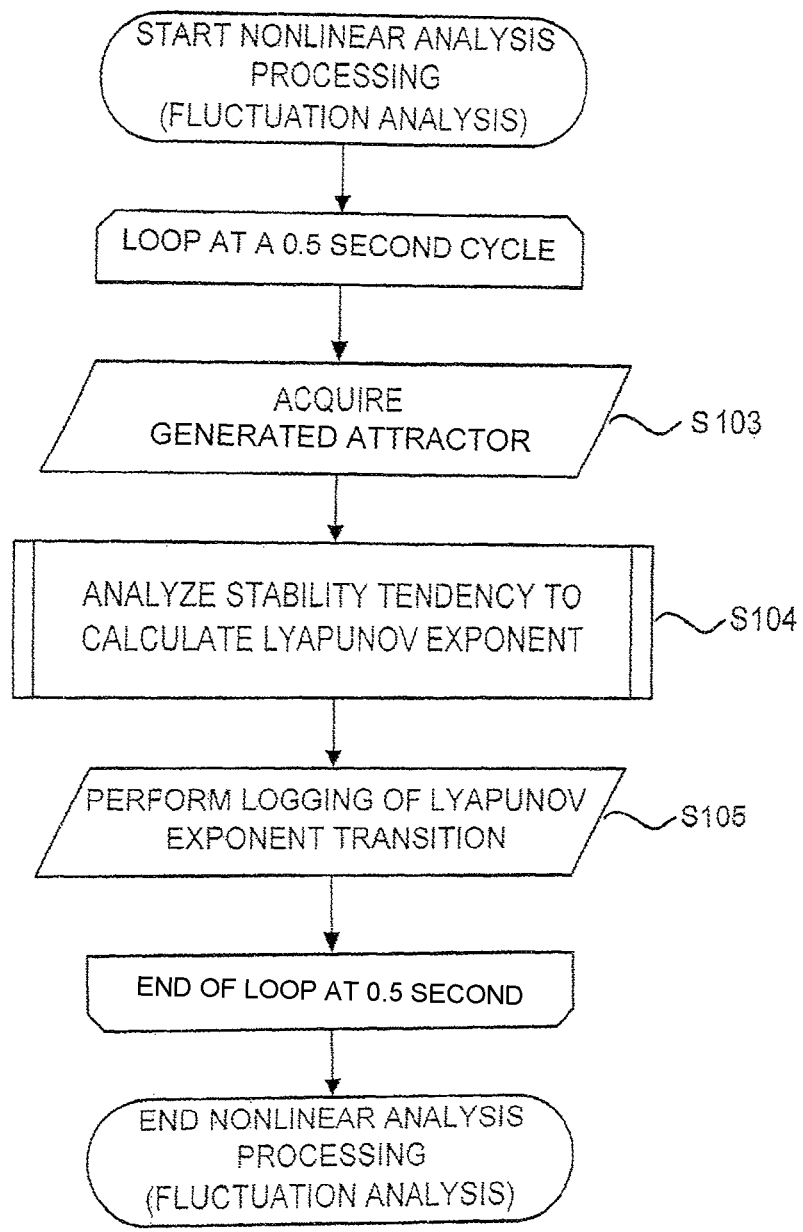
FIG. 4 is a flow chart showing an example (fluctuation analysis processing) of the nonlinear analysis processing in the embodiment of the present invention.

FIG. 3 and FIG. 4 are flow charts showing an example of the nonlinear analysis processing (Step S100 shown in FIG. 2) in the embodiment of the present invention. The nonlinear analysis processing performed in the nonlinear analyzing unit 110 is roughly classified into processing of generating an attractor of the sensing information (FIG. 3) and processing of calculating the Lyapunov exponents using the attractor generated by the attractor generation (FIG. 4).

As shown in FIG. 3, the nonlinear analyzing unit 110 acquires the sensing information detected in the driver's operation detection sensor 191 on the millisecond order (millisecond unit) (Step S101), and then generates an attractor of the value of the acquired sensing information (Step S102). As the sensing information, it is possible to use information (driving operation information) generated when a driver performs usual vehicle driving, such as the accelerator pedal stepping amount detected in the sensor detecting the accelerator pedal stepping amount, for example. Moreover, the generated attractors may be classified according to the vehicle state, such as forward/backward or acceleration/braking. The processing above allows the nonlinear analyzing unit 110 to handle the sensing information as the driving feature amount of a driver, and then generate an attractor thereof.

Next, as shown in FIG. 4, the nonlinear analyzing unit 110 acquires the generated attractor (Step S103), analyzes the stability tendency to the group of the past attractors to calculate the current Lyapunov exponents (Step S104), and then accumulates (logging) the transition (time series data) of the calculated Lyapunov exponents as the log (Step S105). The calculation of the Lyapunov exponents shown in FIG. 4 may be performed at arbitrary cycles and, for example, may be performed at a 0.5 second cycle. When the attractors are classified according to the vehicle state, the Lyapunov exponents may calculated in each classification.

Specific calculation of the fluctuation analysis processing in the embodiment of the present invention can be performed as shown in FIG. 5, for example. FIG. 5 is a view showing an example of a specific calculation method of the fluctuation analysis processing in the embodiment of the present invention. The calculation method of the fluctuation analysis processing is not limited to one shown in FIG. 5. Various researches have been conducted for the nonlinear analysis technique and arbitrary analysis techniques established at present and in the future can be applied to the present invention (see, for example, "Kokomade kita fukuzatsukei kaiseki tool" http://www.ieice.org/cs/csbn/program/papers/04_1_miao.pdf).

Figure 6:
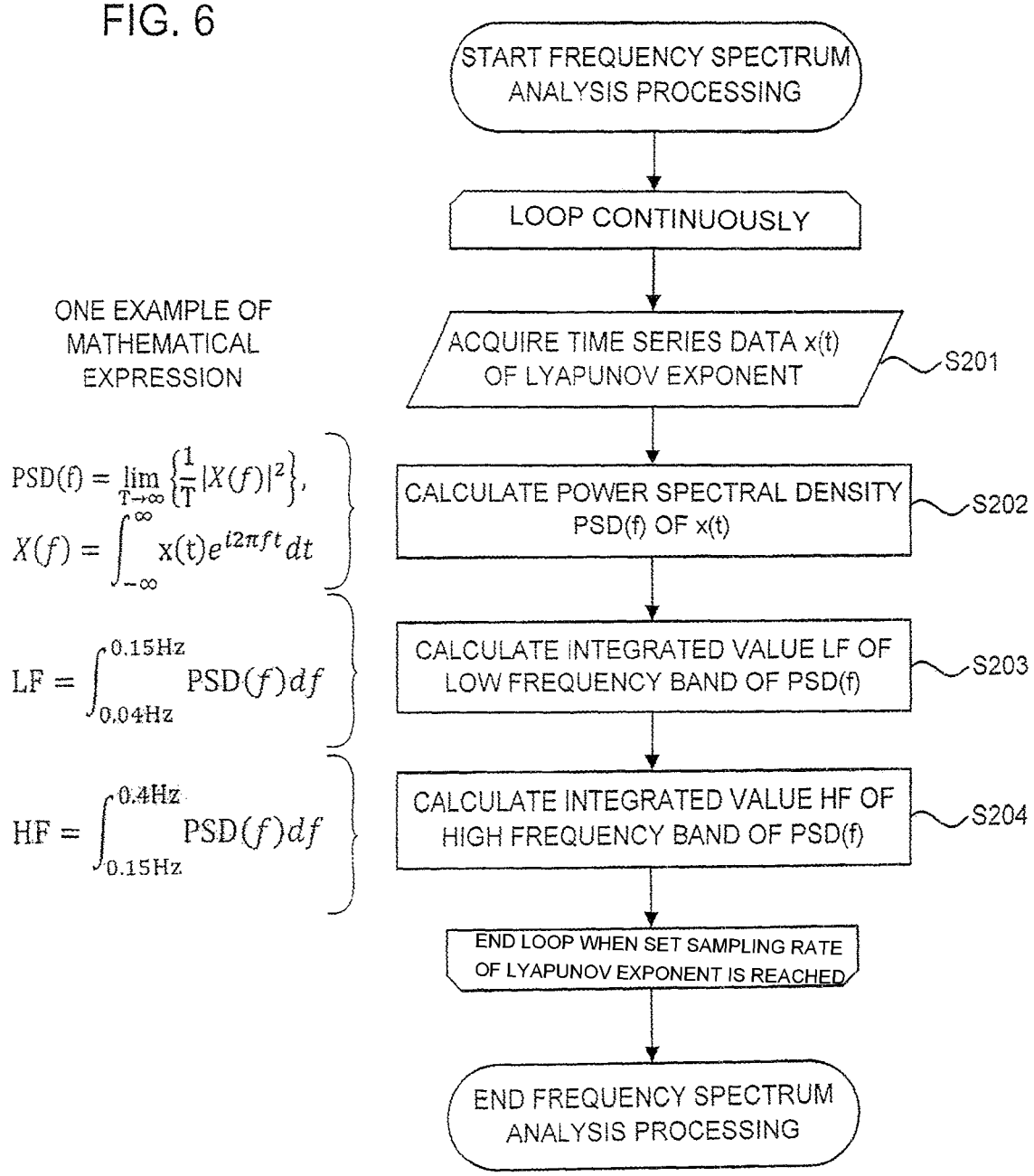
FIG. 6 is a flow chart showing an example of frequency spectrum analysis processing in the embodiment of the present invention.

Next, the frequency spectrum analysis processing (Step S200 shown in FIG. 2) is described. FIG. 6 is a flow chart showing an example of the frequency spectrum analysis processing (Step S200 shown in FIG. 2) in the embodiment of the present invention. The frequency spectrum analyzing unit 120 determines the power spectral density of the time series data of the Lyapunov exponents calculated in the nonlinear analyzing unit 110, and then calculates an integrated value LF of a low frequency band and an integrated value HF of a high frequency band.

In FIG. 6, the frequency spectrum analyzing unit 120 first acquires time series data x(t) of the Lyapunov exponents calculated in the nonlinear analyzing unit 110 (Step S201). The sampling rate of the Lyapunov exponents can be arbitrarily set. For example, a description is given taking the case where values within the range of the sampling rate=10 seconds (0.1 Hz) are acquired as an example about the Lyapunov exponents calculated at a 0.5 second cycle (2 Hz). In this case, the frequency spectrum analyzing unit 120 acquires 20 Lyapunov exponents arranged in time series from the time series data of the Lyapunov exponents x(t) in Step S201.

Figure 7:
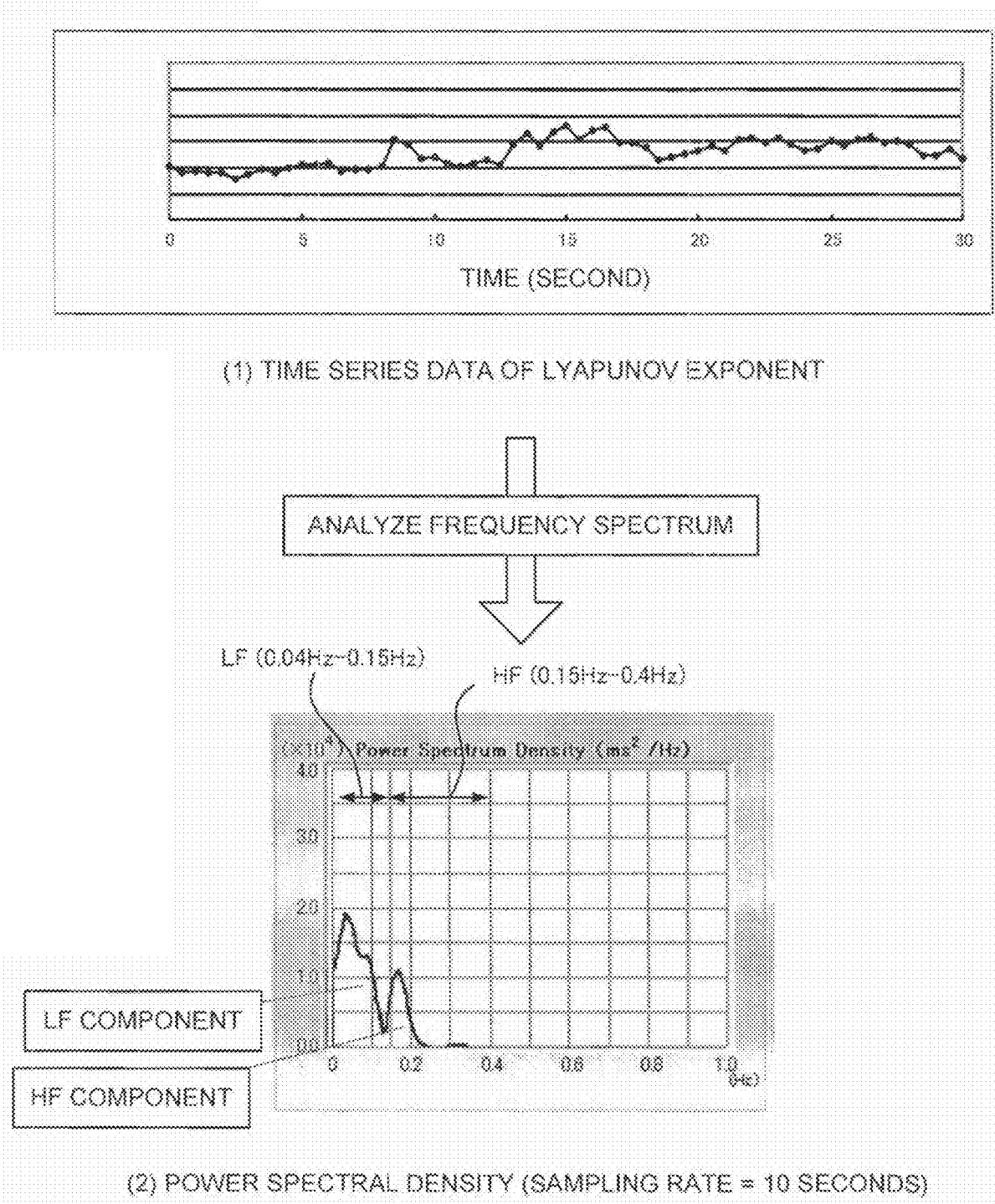
FIG. 7 is a view showing an example of power spectral density calculated by the frequency spectrum analysis processing in the embodiment of the present invention.

Subsequently, the frequency spectrum analyzing unit 120 calculates the power spectral density PSD(f) of the time series data x(t) of the acquired Lyapunov exponents (Step S202). The power spectral density is expressed in FIG. 6 as an example of a mathematical expression (for example, the range of the frequency f is set to 0 Hz to 1 Hz.). For a calculation method therefor, the same method performed in a conventional frequency spectrum analyzing technique may be used. As a result, when the time series data of the Lyapunov exponents as shown in FIG. 7(1), for example, is present, a frequency distribution of the power spectral density can be obtained as shown in FIG. 7(2) by calculating the power spectral density about the amplitude fluctuations of the Lyapunov exponents located within the range of a predetermined sampling rate (for example, 10 seconds).

Then, the frequency spectrum analyzing unit 120 calculates the integrated value LF of the low frequency band of the obtained power spectral density PSD(f) (Step S203), and then further calculates the integrated value HF of the high frequency band of the power spectral density PSD(f) (Step S204). The low frequency band is present on the low frequency side relative to the high frequency band but both the bands may be overlapped with each other. The present inventors have made an attempt to perform various settings for each range of the low frequency band and the high frequency band and have found that an effective result is obtained when the low frequency band is set to 0.04 Hz to 0.15 Hz and the high frequency band is set to 0.15 Hz to 0.4 Hz at present. However, the present invention is not limited to these values.

Moreover, the frequency spectrum analyzing unit 120 calculates the integrated value LF of the low frequency band of the power spectral density PSD(f) and the integrated value HF of the high frequency band of the power spectral density PSD(f) while shifting the time series data x(t) of the power spectral density to be sampled along a time series to thereby perform output at a predetermined sampling rate (for example, 10 seconds) interval. The frequency spectrum analyzing unit 120 may calculate and output a ratio (LF/HF) of the integrated value LF and the integrated value HF to be used in driver's tension level determination processing described later. The present inventors have found, by actually conducting an experiment using a test subject, that the active state of the sympathetic nerve of the test subject (driver) has a correlation with the ratio (LF/HF) of the integrated value LF and the integrated value HF and the active state of the parasympathetic nerve of the test subject (driver) has a correlation with the integrated value HF. More specifically, the ratio (LF/HF) of the integrated value LF and the integrated value HF can be used as the index of the active state of the sympathetic nerve of the test subject (driver) and the integrated value HF can be used as the index of the active state of the parasympathetic nerve of the test subject (driver). Herein, it is supposed that the active state of the sympathetic nerve of the test subject (driver) has a correlation with the ratio (LF/HF) of the integrated value LF and the integrated value HF but it can be supposed that the active state of the sympathetic nerve of the test subject (driver) has a correlation with only the integrated value LF and it can be considered that the active state is simply dependent on only the integrated value LF.

Next, the driver's tension level determination processing (Step S300 shown in FIG. 2) is described. FIG. 8 is a flow chart showing an example of the driver's tension level determination processing (Step S300 shown in FIG. 2) in the embodiment of the present invention. In FIG. 8, the driver's tension level determining unit 130 acquires the integrated value LF of the low frequency band of the power spectral density PSD(f) (or the ratio of the integrated value LF and the integrated value HF) and the integrated value HF of the high frequency band of the power spectral density PSD(f) (Step S301), the power spectral density PSD(f) being output from the frequency spectrum analyzing unit 120 at a predetermined sampling rate (for example, 10 second interval)

Subsequently, the driver's tension level determining unit 130 normalizes the time series data of each of LF/HF and HF (Step S302), and then determines differential time series data of each of the normalized LF/HF and the normalized HF and also, in order to obtain the waveform data peak, performs smoothing of these differential time series data using smoothing differentiation (Step S303).

Then, the driver's tension level determining unit 130 calculates a difference (Differentiation time series data of normalized LF/HF—Differentiation time series data of normalized HF) between the differential time series data of the normalized LF/HF and the differential time series data of the normalized HF calculated in Step S303 (Step S304). As the index of the driver's tension level, the calculation result obtained by the driver's tension level determining unit 130 (Difference between the differential time series data of the normalized LF/HF and the differential time series data of the normalized HF, i.e., "Differentiation time series data of the normalized LF/HF—Differentiation time series data of the normalized HF") is usable. The calculation result shows that, when the difference is large, the tension level of the test subject (driver) is in a state where a tension is excessively high (excessive tension state) and, when the difference is small, the tension level of the test subject (driver) is in a state where a tension is insufficient (insufficient tension state). As described above, it can be supposed that the active state of the sympathetic nerve of the test subject (driver) is simply dependent on only the integrated value LF. In this case, as the calculation result obtained by the driver's tension level determining unit 130, the differential time series data of the normalized LF may be obtained and the calculation relevant to the integrated value HF can be omitted.

In the embodiment of the present invention, at least the three evaluation levels of the moderate tension state (Lv0: Moderate tension state to vehicle driving), the excessive tension state (Lv1) in which the tension level is higher than that of the moderate tension state, and the low insufficient tension state (Lv−1) in which the tension level is lower than that of the moderate tension state can be provided for the driver's tension level (tension state degree) in vehicle driving based on the calculation result obtained by the driver's tension level determining unit 130.

The driver's tension level determining unit 130 can determine that, when the calculation result is larger than a predetermined first threshold value, the driver is in the excessive tension state and that, when the calculation result is smaller than a predetermined second threshold value (value smaller than the first threshold value), the driver is in the insufficient tension state, and then output the determination result (Step S305). For the first and second threshold values, general threshold values determined by conducting trial experiments to a large number of test subjects (drivers) are usable, for example, and a threshold value peculiar to each test subject (each driver) can also be determined by learning as described later.

Figure 9:
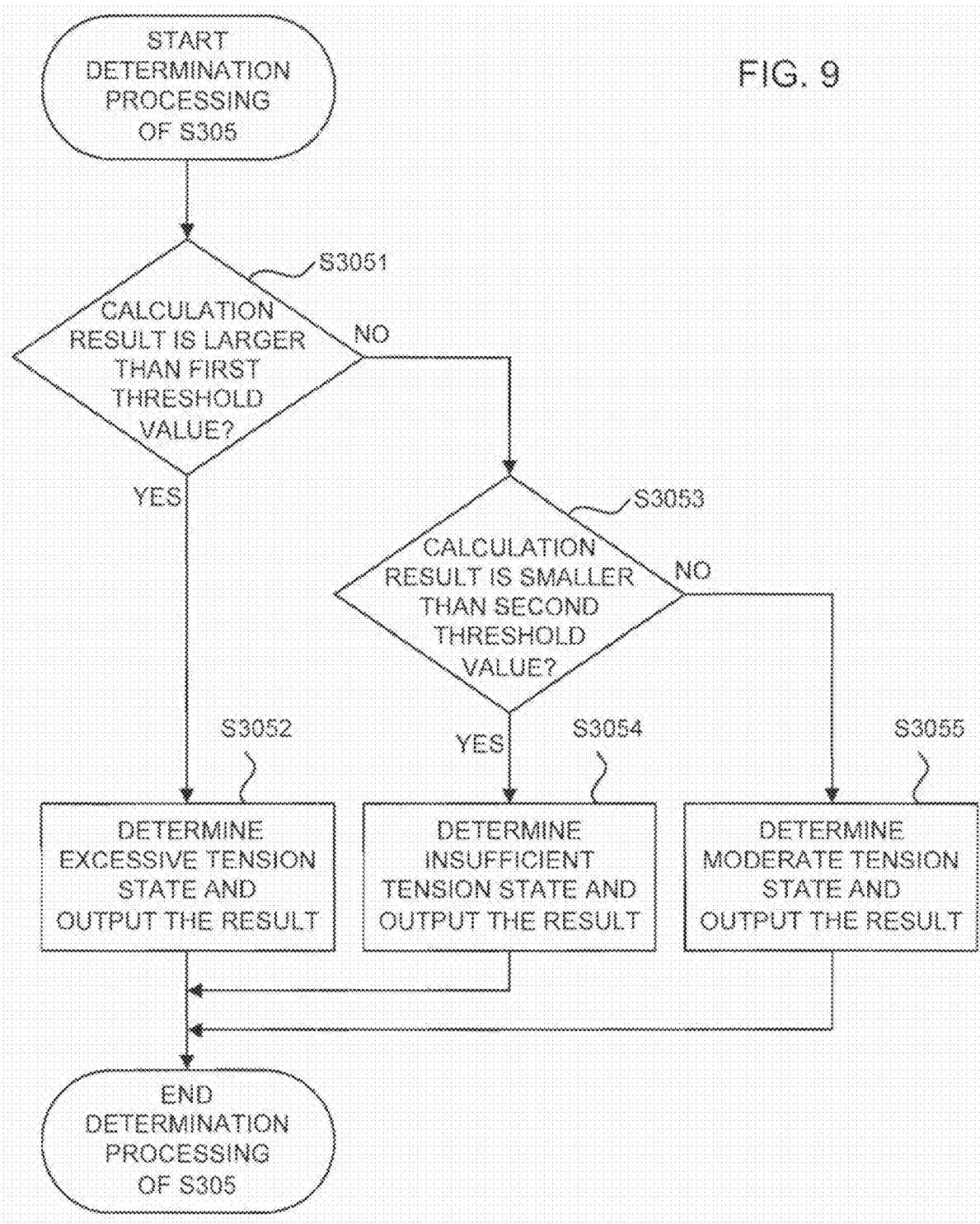
FIG. 9 is a flow chart showing an example of determination processing (Step S305 shown in FIG. 8) performed in the driver's tension level determination processing in the embodiment of the present invention.

Hereinafter, an example of the determination processing in the step S305 is described with reference to FIG. 9. FIG. 9 is a flow chart showing an example of the determination processing (Step S305 shown in FIG. 8) performed in the driver's tension level determination processing in the embodiment of the present invention. In FIG. 9, the driver's tension level determining unit 130 determines whether the calculation result of Step S304 is larger than the first threshold value (Step S3051). When the calculation result of Step S304 is larger than the first threshold value, the drivers tension level determining unit 130 determines that the driver is in the excessive tension state, and then outputs the determination result.

When the calculation result of Step S304 is equal to or smaller than the first threshold value, the driver's tension level determining unit 130 determines whether the calculation result of Step S304 is smaller than the second threshold value (Step S3053). When the calculation result of Step S304 is smaller than the second threshold value, the driver's tension level determining unit 130 determines that the driver is in the insufficient tension state, and then outputs the determination result (Step S3054). On the other hand, when the calculation result of Step S304 is equal to or larger than the second threshold value (and when the calculation result of Step S304 is equal to or smaller than the first threshold value), the driver's tension level determining unit 130 determines that the driver is in the moderate tension state, and then outputs the determination result (Step S3055). As described above, it is determined that the driver is in the excessive tension state when the calculation result of Step S304 is larger than the first threshold value, it is determined that the driver is in the insufficient tension state when the calculation result of Step S304 is smaller than the second threshold value, and it is determined that the driver is in the moderate tension state when the calculation result of Step S304 is equal to or smaller than the first threshold value and is equal to or larger than the second threshold value.

As described above, for the first and second threshold values, general threshold values determined by conducting trial experiments to a large number of test subjects (drivers) are usable, for example. Specifically, a large number of test subjects are made to actually drive a vehicle, and then the calculation results of Step S304 described above are obtained from the operation amounts (for example, the accelerator pedal stepping amount) relating to the driving by the test subjects and the tension level reported by the test subjects (the test subjects subjectively report the tension level which the test subjects feel) or the measurement results of the tension level by a biosensor measuring the cardiac rate, the blood pressure, and the like are obtained, whereby the first and second threshold values serving as the general standard for determining the tension levels of the test subjects (drivers) can be determined.

FIG. 10 shows an example of a graph for determining the first and second threshold values serving as the standard for determining the driver's tension level in the embodiment of the present invention. The vertical axis of the graph shown in FIG. 10 represents the frequency of the tension level and the horizontal axis represents the calculation result (calculation result of Step S304) obtained by the driver's tension level determining unit 130 based on the accelerator pedal stepping amount. The graph of FIG. 10 is a frequency distribution (histogram) showing the calculation result (horizontal axis) obtained from a certain accelerator pedal stepping amount obtained by making a large number of test subjects actually drive a vehicle and the frequency of the tension level (Excessive tension, Insufficient tension, Moderate tension) of the test subjects at that time. For example, the graph shows that, when the calculation result of Step S304 is small, the frequency where the driver shows the insufficient tension state is high, when the calculation result of Step S304 is an intermediate level, the frequency where the driver shows the moderate tension state is high, and, when the calculation result of Step S304 is large, the frequency where the driver shows the excessive tension state is high.

In the histogram shown in FIG. 10, the value of the horizontal axis specified by the intersection of the frequency distribution of the excessive tension state and the frequency distribution of the moderate tension state is possibly defined as the threshold value (first threshold value) for determining the boundary between the excessive tension state and the moderate tension state and the value of the horizontal axis specified by the intersection of the frequency distribution of the moderate tension state and the frequency distribution of the insufficient tension state is possibly defined as the threshold value (second threshold value) for determining the boundary between the moderate tension state and the insufficient tension state. The range where the calculation result of Step S304 is larger than the first threshold value can be set as the excessive tension state, the range where the calculation result of Step S304 is smaller than the second threshold value can be set as the insufficient tension state, and the range where the calculation result of Step S304 is equal to or smaller than the first threshold value and is equal to or larger than the second threshold value can be set as the moderate tension state. Herein, the aspect in which the tension state is classified into three evaluation levels of the excessive tension state (Lv1), the moderate tension state (Lv0), and the insufficient tension state (Lv−1), is described but the number of the levels to classify the evaluation levels can be arbitrarily set. Alternatively, the evaluation level may be expressed by numerical values. For example, the case where a driver is in the excessive tension state may be expressed as "the level exceeds Lv1 (Level 1)", "the level reaches Lv1 (Level 1)", or the like.

The first and second threshold values peculiar to each test subject (each driver) can be determined by learning as described above. Specifically, a certain specific test subject is made to actually drive a vehicle, and then the calculation result of Step S304 described above is obtained from the operation amounts (for example, the accelerator pedal stepping amount) relating to the driving by the certain specific test subject and the tension level reported by the test subject (the test subject subjectively reports the tension level which the test subject feels) or the measurement results of the tension level obtained by a biosensor measuring the cardiac rate, the blood pressure, and the like are obtained, whereby the first and second threshold values serving as the standard for determining the tension level of the test subject (driver) can be determined.

The present invention has proposed a method for determining a suitable threshold value for determining the tension level of a specific test subject (driver) by conducting ROC (Receiver Operating Characteristic) analysis. Hereinafter, an evaluation experiment actually carried out based on data obtained by actual driving by a specific test subject (driver) is described.

In this evaluation experiment, in order to conduct the analysis using a ROC curve, the calculation result (calculation result of Step S304 described above) obtained from the access pedal stepping amount in driving obtained by making a specific test subject (driver) actually drive a vehicle two or more times and the subjectivity of the tension level in the driving by the specific test subject (subjective tension level which the test subject felt) are used, FIG. 11A shows a graph showing the calculation result obtained from the access pedal stepping amount in one driving of the specific test subject (driver). FIG. 11B shows a graph showing the subjectivity of the tension level which the specific test subject felt in the driving. The horizontal axis of the graph shown in FIG. 11A represents time and the vertical axis represents the calculation result value. The horizontal axis of the graph shown in FIG. 11B represents time and the vertical axis represents the subjectivity of the tension level which the specific test subject felt. In this evaluation experiment, the excessive tension state of the test subject is investigated. The tension state degree is classified into four levels of Lv0 to 3 (Levels 0 to 3) of a state where the test subject does not feel a tension (Lv0) and excessive tension states (the excessive tension states are classified into Lv1 to 3 according to the degree and the level rises according to the severity). The specific test subject is made to record the degree of the tension level which the test subject felt every several minutes. More specifically, Lv0 (Level 0) represents the state where the test subject does not feel a tension, Lv1 (Level 1) represents the state where the test subject slightly feels a tension, Lv2 (Level 2) represents the state where the test subject considerably feels a tension, and Lv3 (Level 3) represents the state where the test subject strongly feels a tension.

By setting a certain threshold value to the calculation result obtained from the access pedal stepping amount shown in FIG. 11A, the tension level of the test subject can be estimated. FIG. 12A shows the state where the threshold values of Lv0 to 3 (Levels 0 to 3) are set to specific calculation result values in the graph shown in FIG. 11A. By setting a certain threshold value (first threshold value) to the calculation result shown in FIG. 11A as shown in FIG. 12A, the evaluation level can be estimated from the calculation result. As an example, when the calculation result value obtained from the access pedal stepping amount exceeds the threshold value level, it can be considered that the tension level of the test subject is on the threshold value level.

On the other hand, the subjectivity of the tension level which the test subject felt in driving is obtained as shown in FIG. 11B. The subjectivity of the driver is set as a correct value, and the degree that the evaluation level estimated from the threshold values set as shown in FIG. 12A matches the correct value (the degree where the correct state can be correctly estimated) can be determined. The subjectivities of the driver surrounded by the thick frames in FIG. 12B show portions where the evaluation level estimated from the threshold values set in FIG. 12A matches the correct value (i.e., portions where the correct state is obtained in FIG. 12A)). Thus, based on the calculation result (FIG. 11A) and the correct value (FIG. 11B) obtained by one driving by the specific test subject (driver), the probability (the percentage where the calculation result matches the correct value) in setting a certain threshold value can be obtained. In order to conduct the analysis using the ROC curve, when the probability where the tension state is correctly estimated is determined, it is desirable to simultaneously also determine the probability where a non-tension state is correctly estimated.

In the embodiment of the present invention, the probability obtained in the state where a certain threshold value is set is plotted in the space where the ROC curve is to be created. Specifically, the probability where the tension state is correctly estimated is defined as Sensitivity and the probability where a non-tension state is correctly estimated is defined as Specificity, and the point of (Sensitivity, 1-Specificity) obtained in the state where a certain threshold value is set is plotted in the space where the vertical axis represents Sensitivity and the horizontal axis represents 1-Specificity.

The probability obtained as described above is dependent on the threshold value set to the calculation result. More specifically, it should be noted that, when a different threshold value is set to the calculation result, a different probability is obtained. For example, FIG. 13A shows the state where the threshold values set in FIG. 12A are changed and the threshold value scale (width between the threshold values) is narrowed. FIG. 13B is a graph showing the correct value corresponding to FIG. 13A. As can be easily understood from the comparison with FIG. 12B, when the threshold values are changed, the position and the probability where the calculation result matches the correct value are also changed.

Figure 14:
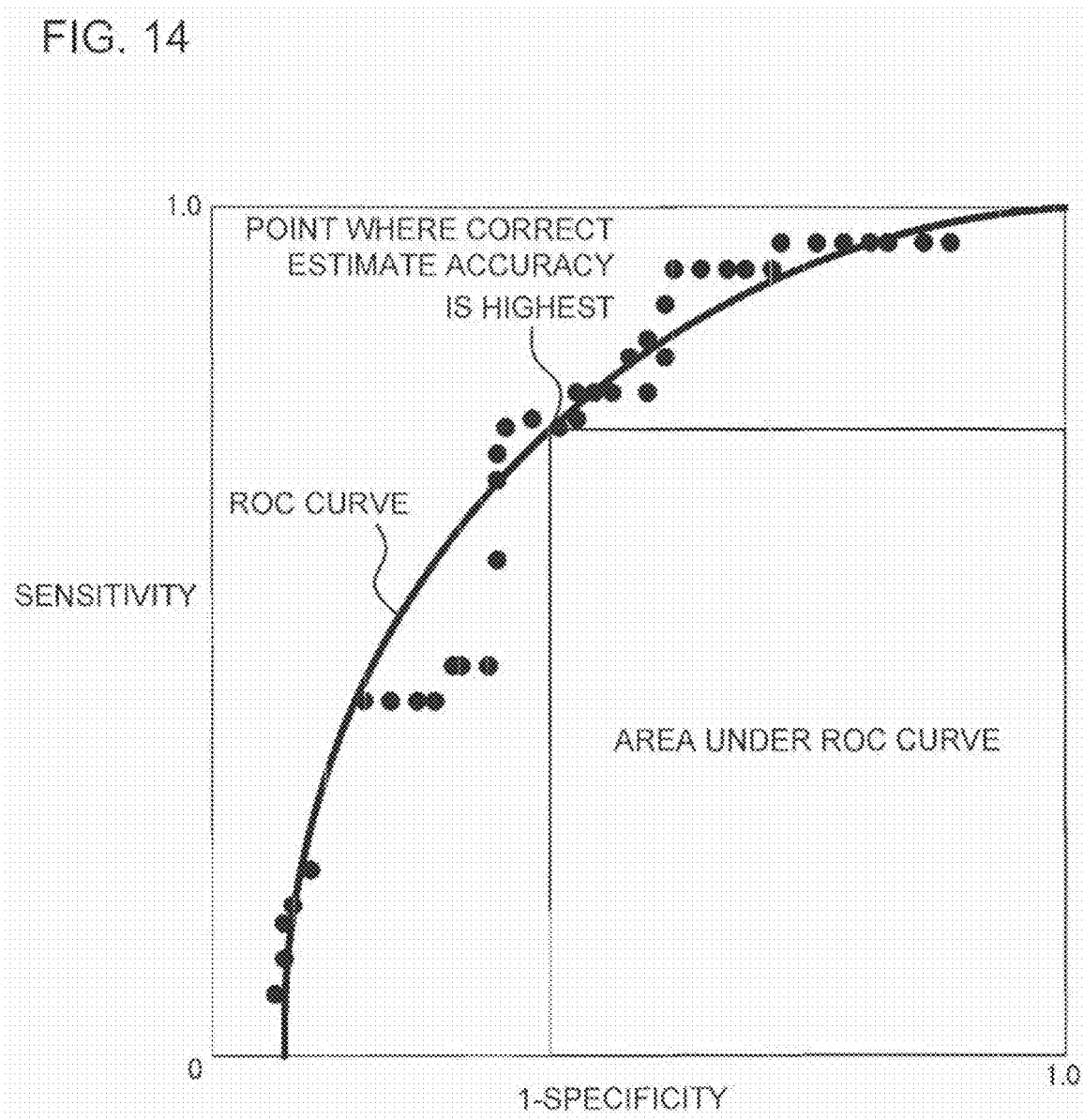
FIG. 14 is a view showing an example of ROC analysis results in the embodiment of the present invention and is a view showing the state where the probabilities obtained corresponding to various threshold value settings are plotted as points of (Sensitivity, 1-Specificity).

FIG. 14 shows the state where the probabilities obtained corresponding to various threshold value settings are plotted as the point of (Sensitivity, 1-Specificity) in the space where the sensitivity is plotted on the vertical axis and 1-specificity is plotted on the horizontal axis while changing the threshold values as described above. When the results of two or more times of vehicle driving are obtained, the probabilities (points of (Sensitivity, 1-Specificity) obtained while setting various threshold values) obtained by the similar method may be plotted in the same space.

The ROC curve can be created from the points plotted in the space where the vertical axis represents Sensitivity and the horizontal axis represents 1-Specificity based on a technique relating to conventional ROC analysis. In the ROC analysis, the point on the ROC curve where the area (Area under the ROC curve) of a rectangular shape defined between the points of (Sensitivity, 1-Specificity)=(0, 1) can be regarded as the value where the correct estimate accuracy is the highest. For example, by regarding the condition (preset value of a threshold value) where a point plotted near the point on the ROC curve where the area under the ROC curve is the maximum is obtained as one reflecting the characteristics relating to a tension of the test subject (driver) most, a suitable threshold value serving as the standard for determining the tension level of the test subject (driver) can be determined in the determination of the tension level in vehicle driving. The characteristics relating to the tension of the test subject (driver) show the tension state degree in a usual state, the tension state degree in performing a special operation, such as driving, and the like. Each driver has a different characteristic, such as a test subject (driver) with a characteristic of easily feeling a tension and a test subject (driver) with a characteristic of rarely feeling a tension. The characteristics relating to the tension of each driver is different in each driver. For example, the zone of the moderate tension state, i.e., the boundary where the tension level enters Lv1 of the excessive tension state from Lv0 of the moderate tension state and the boundary where the tension level enters Lv−1 of the insufficient tension state from Lv0 of the moderate tension state are different in each driver, and therefore, the boundary corresponding to each driver can be learned from the state of the autonomic nerves in daily safe driving in the past of the driver (i.e., the driving operation amounts in daily safe driving). The driver's tension level determining apparatus 100 may have a configuration (a learning unit and a threshold value correction unit) learning the characteristics relating to the tension of each driver and, for example, may be configured so that the driving operation amounts in daily safe driving of a driver are monitored, and then a predetermined threshold value (for example, a threshold value set in factory shipping and a general threshold value obtained from trial experiments performed by a large number of test subjects) may be corrected to a threshold value peculiar to a driver based on the monitored result. Thus, by reflecting the characteristics relating to a tension of each test subject (driver) in the determination of the tension level in vehicle driving, the determination accuracy of the tension level in vehicle driving can be improved.

Since the sensitivity and the specificity have a trade-off relationship in the ROC curve, a threshold value which intentionally lowers the sensitivity (probability where the tension state is correctly estimated) to thereby intentionally raise the specificity (probability where a non-tension state is correctly estimated) may be adopted for the point on the ROC curve where the area under the ROC curve is the maximum or, conversely, a threshold value which intentionally raises the sensitivity (probability where the tension state is correctly estimated) to thereby intentionally lower the specificity (probability where a non-tension state is correctly estimated) may be adopted therefor.

In the evaluation experiment described above, the threshold value relating to the determination of the excessive tension state of a test subject is determined by the analysis using the ROC curve but, also when determining the threshold value relating to the determination of the insufficient tension state of a test subject, the same method is usable.

The driver's tension level determining unit 130 can determine and output that the driver's tension level is any one of the excessively high tension, the moderate tension, or the insufficient tension and the output result may be utilized in various devices or methods. For example, when it is determined that the driver is in the excessive tension state, music or scent relaxing a driver may be played/given in a vehicle. For example, when it is determined that the driver is in the insufficient tension state, a stimulus may be given to the driver by sound, light, or the like or music or scent increasing the concentration may be played/given in a vehicle.

As described above, according to the embodiment of the present invention, the driver's tension level in vehicle driving can be determined in detail by classifying the driver's tension level in vehicle driving according to the at least three evaluation levels of the moderate tension state (moderate tension state to vehicle driving), the excessive tension state where the tension level is higher than that of the moderate tension level, and the insufficient tension state where the tension level is lower than that of the moderate tension level. Moreover, according to the embodiment of the present invention, the tension level can be determined at higher accuracy by determining the tension level corresponding to the characteristics of each driver.

INDUSTRIAL APPLICABILITY

The present invention has an effect that the driver's tension level in vehicle driving can be determined in detail with a simple configuration based on information relating to the operation amounts of usual vehicle driving operations (operations of an accelerator pedal, a brake pedal, a handle, and the like) of a driver and can be applied to a technique of determining the driver's tension level in vehicle driving.

What is claimed is:

1. An apparatus for determining a tension state degree of a driver's tension level when the driver is driving a vehicle, the apparatus including a computer having a processor and sensors;
   wherein the sensors monitor and acquire driving operation data relating to how the driver operates the vehicle; and
   wherein the processor is configured to execute the following operations of:
      calculating a Lyapunov exponent about the driving operation data by performing nonlinear analysis processing;
      calculating a power spectral density of time series data of the Lyapunov exponent, and then calculating an integrated value of a predetermined low frequency band in the calculated power spectral density; and
      determining that the tension state degree of the driver is any one of an excessive tension state, a moderate tension state, and an insufficient tension state using the integrated value of the predetermined low frequency band,
   wherein the processor further executes
   a determining operation by using the integrated value of the predetermined low frequency band as an index of an active state of a sympathetic nerve of the driver, and,
      when a value obtained based on the integrated value of the predetermined low frequency band is larger than a first threshold value, determining that the tension state degree of the driver is in the excessive tension state,
      when the value obtained based on the integrated value of the predetermined low frequency band is smaller than a second threshold value, determining that the tension state degree of the driver is in the insufficient tension state, and,
      when the value obtained based on the integrated value of the predetermined low frequency band is equal to or smaller than the first threshold value and is equal to or larger than the second threshold value, determining that the tension state degree of the driver is in the moderate tension state, and
   wherein
   the first threshold value and the second threshold value are determined, by a receiver operating characteristic analysis method, based on a probability representing a first level matches a second level, the first level corresponding to the integrated value of the predetermined low frequency band which varies with time, the second level being a tension level which the driver feels in driving, and
   wherein, depending on the determined tension state of the driver, an appropriate stimulus is provided to the driver in the vehicle.

2. Apparatus according to claim 1, wherein operation data relating to any one of an accelerator pedal, a brake pedal, and a handle operated by the driver when driving the vehicle is used as the driving operation data relating to a driving operation of the driver.

3. A method of determining a tension state degree of tension level of a driver when the driver is driving a vehicle by using a driver's tension level determining apparatus that includes sensors, a nonlinear analyzing means, a frequency spectrum analyzing means and a driver's tension level determining means, the method comprising:
   using the sensors to monitor and acquire driving operation data relating to how the driver is operating the vehicle;
   utilizing the nonlinear analyzing means for calculating a Lyapunov exponent about the driving operation data by performing nonlinear analysis processing;
   utilizing the frequency spectrum analyzing means for calculating a power spectral density of time series data of the Lyapunov exponent, and then calculating an integrated value of a predetermined low frequency band in the calculated power spectral density; and
   utilizing the driver's tension level determining means for determining that the tension state degree of the driver is any one of an excessive tension state, a moderate tension state, and an insufficient tension state using the integrated value of the predetermined low frequency band,
   wherein
   in the driver's tension level determining means, the integrated value of the predetermined low frequency band is used as an index of an active state of a sympathetic nerve of the driver, and,
      when a value obtained based on the integrated value of the predetermined low frequency band is larger than a first threshold value, it is determined that the tension state degree of the driver is in the excessive tension state,
      when the value obtained based on the integrated value of the predetermined low frequency band is smaller than a second threshold value, it is determined that the tension state degree of the driver is in the insufficient tension state, and,
      when the value obtained based on the integrated value of the predetermined low frequency band is equal to or smaller than the first threshold value and is equal to or larger than the second threshold value, it is determined the tension state degree of the driver is in the moderate tension state, and
   wherein
   the first threshold value and the second threshold value are determined, by a receiver operating characteristic analysis method, based on a probability representing a first level matches a second level, the first level corresponding to the integrated value of the predetermined low frequency band which varies with time, the second level being a tension level which the driver feels in driving, and depending on the determined tension state of the driver, providing an appropriate stimulus to the driver in the vehicle.

4. The driver's tension level determining method according to claim 3, wherein operation data relating to any one of an accelerator pedal, a brake pedal, and a handle operated by the driver when driving the vehicle is used as the driving operation data relating to a driving operation of the driver.

5. Apparatus for determining a tension state degree of a driver's tension level when the driver is driving a vehicle, comprising:

at least one sensor to monitor and acquire driving operation data relating to how the driver operates the vehicle;

a non-linear analyzing unit configured to execute the following processes:

calculate a Lyapunov exponent about the driving operation data by performing nonlinear analysis processing;

calculate a power spectral density of time series data of the Lyapunov exponent, and then calculating an integrated value of a predetermined low frequency band in the calculated power spectral density; and determine that the tension state degree of the driver is any of an excessive tension state, a moderate tension state, and an insufficient tension state using the integrated value of the predetermined low frequency band, a frequency spectrum analyzing unit configured to execute a determine process by using the integrated value of the predetermined low frequency band as an index of an active state of a sympathetic nerve of the driver, and, when a value obtained based on the integrated value of the predetermined low frequency band is larger than a first threshold value, it is determined that the tension state degree of the driver is in the excessive tension state, when the value obtained based on the integrated value of the predetermined low frequency band is smaller than a second threshold value, it is determined that the tension state degree of the driver is in the insufficient tension state, and, when the value obtained based on the integrated value of the predetermined low frequency band is equal to or smaller than the first threshold value and is equal to or larger than the second threshold value, it is determined the tension state degree of the driver is in the moderate tension state, and wherein the first threshold value and the second threshold value are determined, by a receiver operating characteristic analysis method, based on a probability representing a first level matches a second level, the first level corresponding to the integrated value of the predetermined low frequency band which varies with time, the second level being a tension level which the driver feels in driving, and wherein an appropriate stimulus that depends on the determined tension state of the driver is provided to the driver in the vehicle.

6. The apparatus of claim 5, wherein the non-linear analyzing unit and the frequency spectrum analyzing unit are respective processing functions executed by a computer that includes a processor and a memory.

* * * * *